United States Patent [19]
Odenwälder et al.

[11] 4,250,252
[45] Feb. 10, 1981

[54] LIGHT-SENSITIVE COLOR PHOTOGRAPHIC MATERIAL

[75] Inventors: Heinrich Odenwälder; Hans Vetter, both of Cologne; Walter Püschel; Erwin Ranz, both of Leverkusen, all of Fed. Rep. of Germany

[73] Assignee: AGFA-Gevaert, A.G., Leverkusen, Fed. Rep. of Germany

[21] Appl. No.: 619,301

[22] Filed: Oct. 3, 1975

[30] Foreign Application Priority Data

Oct. 9, 1974 [DE] Fed. Rep. of Germany ....... 2448063

[51] Int. Cl.³ .............................................. G03C 1/76
[52] U.S. Cl. .................................... 430/505; 430/445; 430/448; 430/504; 430/544; 430/957
[58] Field of Search ................. 96/76 R, 74, 100, 109, 96/3

[56] References Cited

U.S. PATENT DOCUMENTS

| | | | |
|---|---|---|---|
| 2,353,205 | 7/1944 | Yittum et al. | 96/100 |
| 2,364,675 | 12/1944 | Yittum et al. | 96/100 |
| 2,435,629 | 2/1948 | Jennings | 96/100 |
| 3,844,795 | 10/1974 | Puschel et al. | 96/9 |
| 3,932,185 | 1/1976 | Matsuura | 96/109 |
| 3,936,300 | 2/1976 | Cardone | 96/109 |

FOREIGN PATENT DOCUMENTS 2359295  5/1974  Fed. Rep. of Germany.

*Primary Examiner*—J. Travis Brown
*Attorney, Agent, or Firm*—Connolly & Hutz

[57] ABSTRACT

In a color photographic material wherein by color development there are produced either non-diffusing image dyes or diffusing image dyes (the latter being transferred to an image-receiving layer) the color development is controlled by means of non-diffusing thioether compounds which on color development release a diffusing mercapto compound but do not themselves form a dye. The mercapto compound inhibits the development of the silver halide and the thioether compound has the formula

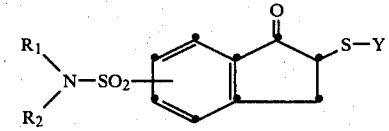

$R_1$ = hydrogen or alkyl with 1–3 carbon atoms
$R_2$ = alkyl with up to 22 carbon atoms the group —S—Y is split off during color development and forms a mercaptane, e.g. 5-mercapto-1-phenyltetrazole, which inhibits the development.

5 Claims, No Drawings

LIGHT-SENSITIVE COLOR PHOTOGRAPHIC MATERIAL

This invention relates to a colour photographic material containing compounds which react with oxidation products of colour developers to release development inhibitors.

It is well known that compounds which react with colour developer oxidation products to release development inhibitors can be incorporated in colour photographic materials. These compounds include, for example, the so-called DIR couplers (DIR=Development inhibitor releasing) which have been described in U.S. Pat. No. 3,227,554. These compounds are colour couplers which contain a thioether substituent in the coupling position; when the colour coupling reaction takes place, this substituent is split off as a diffusible mercapto compound which has development inhibiting properties and therefore influences the subsequent development of silver halide. These DIR couplers improve the properties of colour photographic materials in numerous respects. They are capable of controlling the graininess, sharpness and gradation and therefore can substantially improve colour reproduction as a whole. In this connection, reference is made to the article entitled "Development-Inhibitor-Releasing (DIR) Couplers in Photography" in Photographic Science Engineering 13, 74 (1969).

When these DIR couplers release the development inhibitor they inevitably also give rise to a dye. The DIR coupler used must therefore be carefully chosen to ensure the correct colour balance in a colour photographic material. In particular, one and the same DIR coupler cannot be used in all the colour forming layers of a colour photographic multilayer material since the colour of the dye formed in the reaction generally only corresponds with the image dye of one layer and would increase undesirable side densities of the partial colour image in the other layers.

These disadvantages do not arise if, instead of DIR couplers, compounds are used which react with colour developer oxidation products to release diffusible development inhibitors but which do not at the same time produce a dye. Compounds of this kind, which are known as DIR compounds to distinguish them from the DIR couplers mentioned above, have been described, for example, in U.S. Pat. No. 3,632,345. These compounds are mainly acetophenone derivatives which carry a thioether substituent in the ω-position. This substituent is obviously split off when the compound reacts with oxidation products of colour developers. Another group of development inhibitor compounds which also do not give rise to dyes has been described in German OS No. 2,359,295. These DIR compounds are cycloalkanones which carry a thioether substituent in the α-position relative to the keto group. It has been found, however, that the known DIR compounds are either too unstable under certain operating conditions or insufficiently reactive. In the former case, the development inhibitor is more or less uniformly released and not only in accordance with the image, and this results in a general loss in sensitivity. In the latter case, the inhibitor is split off too slowly and therefore cannot affect the process of development to a sufficient extent.

An object of the present invention is to find new compounds which react with colour developer oxidation products to release development inhibitors without giving rise to permanent dyes in the course of the process and which combine sufficient reactivity with sufficient stability.

Within the class of DIR compounds of the cycloalkanone type mentioned above, one group of compounds has now been found which are considerably superior in their reactivity to all other known DIR compounds. They are indanone derivatives which carry a sulphamyl group in the aromatic ring.

This invention relates to a colour photographic material which contains a thioether compound, preferably one which is non-diffusible, in at least one silver halide emulsion layer or in an associated layer of binder which is not sensitive to light, which thioether compound reacts with the oxidation product of a colour developer compound containing a primary aromatic amino group to release a diffusible substance which inhibits development of the silver halide. The material is characterised in that the thioether compound corresponds to the following formula:

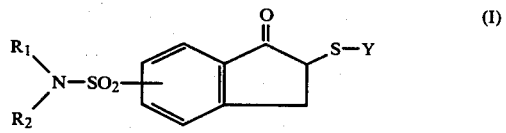

wherein
Y denotes an aliphatic group, an aromatic group or in particular a heterocyclic group such that when it is split off together with the sulphur atom of the thioether bridge it forms a diffusible mercapto compound which inhibits the development of silver halide;
$R_1$ denotes hydrogen or alkyl, preferably with from 1 to 3 C-atoms, e.g. methyl; and
$R_2$ denotes an alkyl group containing up to 22 C-atoms, which may be straight chain or branched and which may contain further substituents such as alkoxy or aryloxy; or an aralkyl group such as benzyl, or an aryl group such as phenyl, preferably a substituted phenyl group which may carry further substituents, e.g. alkyl such as methyl, isopropyl, amyl, isoctyl and dodecyl; cycloalkyl such as cyclopentyl, alkoxy such as methoxy; amino including dialkylamino and acylamino; or sulfo.

The following are examples of aliphatic groups which may be represented by Y:

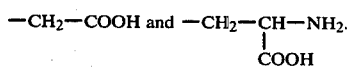

The following are examples of aromatic groups which may be represented by Y: phenyl, carboxyphenyl and nitrophenyl.

The following are examples of heterocyclic groups which may be represented by Y: tetrazolyl, such as 1-phenyltetrazolyl, 1-nitrophenyltetrazolyl, and 1-naphthyltetrazolyl; triazolyl such as 1-phenyl-1,2,4-triazolyl; thiadiazolyl such as 2-phenylamino-1,3,4-thiadiazolyl; oxadiazolyl; thiazolyl, including benzothiazolyl and naphthiazolyl; oxazolyl, including benzoxazolyl and naphthoxazolyl, for example 7-sulphonaphtho[2,3-d]oxazolyl; pyrimidyl such as 4-methyl-6-aminopyrimidyl or 4-methyl-6-hydroxypryimidyl; or triazinyl such as thiadiazolotriazinyl.

Compounds in which $R_2$ contains a photographically inert group which confers resistance to diffusion are preferred.

By groups which confer diffusion resistance are meant those which enable the compounds according to the invention to be incorporated without diffusion in the hydrophilic colloids normally used in photographic materials. Particularly suitable for this purpose are organic groups which may generally contain straight chain or branched chain aliphatic groups and optionally also carbocyclic or heterocyclic aromatic groups. The aliphatic portion of these groups generally contains from 8 to 20 C-atoms. The groups are attached to the remainder of the molecule either directly or indirectly, for example through one of the following groups: —CONH—, —SO$_2$NH—, —CO—, —SO$_2$— or —NR— (R=hydrogen or alkyl), —O— or —S—.

The group which confers diffusion resistance may in addition contain groups which confer solubility in water, e.g. sulpho groups or carboxyl groups, and these may also be in an anionic form. Since the diffusion properties depend on the molecular size of the whole compound used, it is in certain cases sufficient, for example if the molecule as a whole is large enough, to use shorter chain groups as the so-called diffusion resistance conferring groups.

Indanone DIR compounds which carry the sulphamyl group in the 5- or 6-position have proved to be particularly suitable. The following are given as examples:

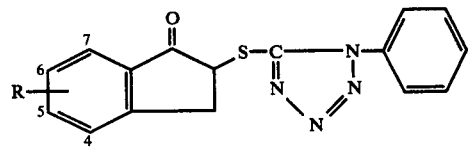

| No. | R | m.p. (°C.) |
| --- | --- | --- |
| 1 | 5-SO$_2$—NH—(CH$_2$)$_{15}$—CH$_3$ | 63–65 |
| 2 | 5-SO$_2$—NH—(CH$_2$)$_3$—O—CH(C$_2$H$_5$)—(CH$_2$)$_3$—CH$_3$ | not crystalline |
| 3 | 6-SO$_2$—NH—(CH$_2$)$_{15}$—CH$_3$ | 144–145 |
| 4 | 5-SO$_2$—N(CH$_3$)—(CH$_2$)$_{17}$—CH$_3$ | 66–70 |
| 5 | 5-SO$_2$—NH—C$_6$H$_4$—C$_{12}$H$_{25}$ | |
| 6 | 5-SO$_2$—NH—(CH$_2$)$_4$—O—C$_6$H$_3$(C$_5$H$_{11}$(t))$_2$ | 103–105 |
| 7 | 5-SO$_2$—NH—(CH$_2$)$_{17}$—CH$_3$ | 70–74 |
| 8 | 5-SO$_2$—NH—(CH$_2$)$_{13}$—CH$_3$ | 77–80 |
| 9 | 5-SO$_2$—NH—CH$_2$—CH(C$_2$H$_5$)—(CH$_2$)$_3$—CH$_3$ | 74–76 |
| 10 | 6-SO$_2$—NH—C$_6$H$_2$(CH(CH$_3$)$_2$)$_3$ | 196–198 (decomp.) |
| 11 | 6-SO$_2$—NH—C$_6$H$_2$(CH(CH$_3$)$_2$)$_2$CH$_3$ | 181–184 |
| 12 | 6-SO$_2$—NH—C$_6$H$_3$(cyclopentyl)$_2$ | 196–199 |
| 13 | 6-SO$_2$—NH—C$_6$H$_3$(SO$_3$H)(N(CH$_3$)C$_{18}$H$_{37}$) | 186–188 |

-continued

| No. | R | m.p. (°C.) |
|---|---|---|
| 14 | 6-SO₂—NH—⟨SO₃H, N(CH₃)(C₁₈H₃₇)⟩ | 183–185 |
| 15 | 6-SO₂—NH—(CH₂)₄—O—⟨⟩—C(CH₃)₂—CH₂—C(CH₃)₃ | 139–142 |
| 16 | 6-SO₂—NH—(CH₂)₄—O—⟨C₅H₁₁(iso), C₅H₁₁(iso)⟩ | 159–161 |
| 17 | 6-SO₂—NH—⟨CH₃O, NH—CO—(CH₂)₃—O—⟨C₅H₁₁(tert.), C₅H₁₁(tert.)⟩⟩ | 140–143 |

The indan-1-one-sulphochlorides required as starting materials can be obtained by methods known from the literature. For example, 5-chlorosulphonyl-1-indanone can be obtained by cyclisation of 3-acetaminophenyl-propionic acid in phosphoric acid (Synthesis 1972, 614), saponification to 5-aminoindanone and conversion into the sulphochloride (Houben-Weyl, Vol. IX, page 579 et seq).

The inhibitor group can be introduced by known methods such as those which have been outlined in U.S. Pat. No. 3,632,345, for example by the reaction of a 2-halo-indan-1-one with the sodium salt of the inhibitor.

It is particularly advantageous, however, to introduce the inhibitor group by combining a solution of an indan-1-one in an inert solvent (e.g. CHCl₃ or CCl₄) with a solution of the sulphenyl bromide of the inhibitor, which can be obtained from 1 mol of the inhibitor and 1 mol of bromine in an inert solvent (e.g. CHCl₃ or CCl₄).

The reaction time of the reaction which then follows may be up to 24 hours, depending on the temperature employed, which is preferably between room temperature and the boiling point of the solvent.

Preparation of 5-aminoindanone 20 g of 3-acetaminophenylpropionic acid in 300 g of 84% polyphosphoric acid are heated to 70° C. for 2 hours with stirring, cooled to 50° C. and slowly poured into a mixture of 800 g of ice and 200 ml of water. After one hour's stirring, the precipitate is suction-filtered and washed free from acid with water. The resulting product is boiled under reflux in a mixture of 400 ml of water, 5 g of NaOH and 3 g of active charcoal for one hour and suction-filtered while still hot, and the solution is cooled. The crystals which precipitate are suction-filtered and recrystallised from 400 ml of water with 2 g of active charcoal. Yield after drying: 4 g of 5-aminoindanone, corresponding to 28% of the theoretical yield; m.p. 193°–194° C.

Preparation of indanone-5-sulphochloride 10.7 g of 5-aminoindanone are stirred in a mixture of 20 ml of concentrated hydrochloric acid and 20 ml of water and cooled to −5° C. A solution of 5 g of sodium nitrite in 15 ml of water is added dropwise at this temperature and stirring is continued for 5 minutes after all the solution has been added. The excess nitrons acid is then destroyed with amidosulphonic acid. The diazonium salt solution is added carefully to a mixture, which has been cooled to 10° C., of 70 ml of a 20% by weight solution of SO₂ in glacial acetic acid and a solution of 3 g of CuCl₂ in 5 ml of water while the temperature of the reaction mixture is kept at 10° C. 150 ml of water are added after 10 minutes, and the precipitated indanone-5-sulphochloride is then suction-filtered, washed with water and dried. Yield: 13 g. 10.5 g of pure sulphochloride melting at 110° to 112° C. are obtained after recrystallisation from 400 ml of cyclohexane with 2.5 g of active charcoal.

Preparation of

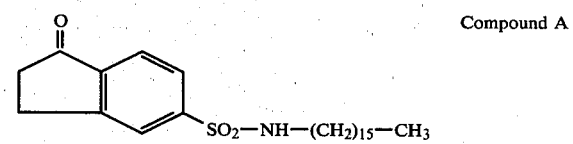

Compound A 16.5 g of hexadecylamine and 6 g of Na₂CO₃ are briefly heated to boiling in 200 ml of acetonitrile. After cooling, 15 g of indanone-5-sulphochloride are introduced and the mixture is boiled under reflux for 30 minutes. After cooling, the product is precipitated with 200 ml of water, suction-filtered and dried. Recrystallisation from 125 ml of ethanol and then from 190 ml of cyclohexane yields 17.4 g of Compound A, corresponding to 61% of the theoretical yield; m.p. 121°–123° C.

Preparation of Compound 1

0.73 ml of bromine are gradually added to 2.5 g of 1-phenyl-5-mercaptotetrazole in 20 ml of chloroform. A solution of 5 g of compound A in 50 ml of chloroform is added to the resulting clear solution and boiled under reflux for 2 hours. The chloroform solution is cooled and extracted twice with 5% by weight sodium carbonate solution and then with water, and the organic phase is dried with $Na_2SO_4$. The solvent is evaporated off under vacuum and the oil remaining behind is crystallised with 10 ml of methanol, suctionfiltered, washed with 5 ml of methanol and dried.

Yield: 4.9 g of compound 1 (86% of the theoretical yield), m.p. 63°–65° C.

The compounds according to the invention are comparable with the known DIR couplers disclosed in U.S. Pat. No. 3,227,554 in the following respects: Like the known couplers, they are non-diffusible thioether compounds which react with colour developer oxidation products to release a diffusible mercaptan which inhibits the development of silver halide. They differ from the known DIR couplers, however, in that they do not undergo a colour coupling reaction, that is to say they do not give rise to a stable dye which remains in the photographic material to affect the finished colour image. The compounds according to the invention may therefore be described as DIR compounds in contrast to the known DIR couplers. According to U.S. Pat. No. 3,148,062, DIR couplers are subdivided into those in which the group which is split off is already capable of acting as an development inhibitor before coupling takes place, and those in which the inhibiting activity is released only when a residue of the molecule is split from the coupling position. In the latter case, the inhibitor is non-preformed. In accordance with this terminology, the compounds according to the invention should therefore be referred to as non-diffusible compounds which react with colour developer oxidation products to release a diffusible, non-preformed development inhibitor.

Compared with the compounds according to U.S. Pat. No. 3,632,345 and German OS No. 2,359,295, the compounds according to the invention are distinguished by their increased reactivity, which is particularly advantageous when development is carried out at a relatively low pH, e.g. at pH 10–11. The DIR compounds according to the invention are still sufficiently active under these conditions.

The DIR compounds according to the invention are particularly suitable for use in colour photographic multilayered materials of the kind in which the silver halide is exposed imagewise and then developed by conventional colour developers, for example by the usual aromatic compounds of the p-phenylenediamine series which contain at least one primary amino group.

The following are examples of suitable colour developers:
N,N-dimethyl-p-phenylenediamine;
N,N-diethyl-p-phenylenediamine;
monomethyl-p-phenylenediamine;
2-amino-5-diethylaminotoluene;
N-butyl-N-ω-sulphobutyl-p-phenylenediamine;
2-amino-5-(N-ethyl-N-β-methanesulphonamidoethylamino)toluene;
N-ethyl-N-β-hydroxyethyl-p-phenylenediamine;
N,N-bis-(β-hydroxyethyl)-p-phenylenediamine;
2-amino-5-(n-ethyl-N-β-hydroxyethylamino)-toluene, Other useful colour developers have been described, for example in J. Amer. Chem. Soc. 73, 3100 (1951).

The developers are usually contained in an alkaline development bath which is used to treat the colour photographic material which has been exposed imagewise. However, the developers may also be contained in one or more layers of the photographic material. In the latter case, the developers may contain groups which confer diffusion resistance and they may be situated in a layer which also contains a diffusion resistant colour coupler or a diffusion resistant dye-giving compound as described, for example, in U.S. Pat. No. 3,705,035. Development then requires only an alkaline activator solution containing an auxiliary developer, for example phenidon (1-phenylpyrazolidone-(3)). The oxidation product of the colour developer produced in the course of development reacts with the non-diffusible colour coupler to form a non-diffusible image dye or it reacts with the non-diffusible dye-giving compound to form an imagewise distribution of diffusible dyes which can be transferred to an image-receiving layer. At the same time, the oxidation product of the colour developer reacts with the non-diffusible DIR compounds according to the invention, which are also present, to release diffusible inhibitor molecules, but no permanent dye is produced from the remaining part of the molecule of the DIR compound.

At least one of the layers of the colour photographic multilayered material according to the invention contains a compound according to the formula (I). The DIR compound may be incorporated in a light-sensitive silver halide emulsion layer or in a hydrophilic layer of binder which is associated with such a light-sensitive silver halide emulsion layer and which need not itself be sensitive to light. In this context, a layer is regarded as being associated if it is spatially related to the light-sensitive silver halide emulsion layer in such a way that, when the silver halide emulsion layer is developed, significant quantities of colour developer oxidation products can be found in the associated layer owing to diffusion from the light-sensitive silver halide emulsion layer.

A light-sensitive silver halide emulsion layer of the material of the present invention may consist of two or more partial layers having the same or different sensitivities and containing the same or different color couplers. A DIR compound of the present invention may be present in each or in only one of such partial layers.

The concentration of the DIR compound according to the invention in the layer containing it may vary within wide limits, e.g. between $0.1 \cdot 10^{-3}$ and $40 \cdot 10^{-3}$ mol per kg of silver halide emulsion and in the associated layers of binder, for example between $0.1 \cdot 10^{-3}$ and $10 \cdot 10^{-3}$ mol per gram of binder. The quantity depends on the particular purpose, on the particular silver halide emulsion used and on whether the DIR compound is contained in the silver halide emulsion layer or in a layer of binder which is not light-sensitive. The upper limit generally lies in the region of the concentrations used for colour couplers in photographic layers. However, such a limit need not be strictly observed since the DIR compounds according to the invention do not contribute to the formation of the colour image.

The colour developer oxidation products are absorbed by the reaction with the compounds according to the invention to form colourless products and in this way removed from the possibility of any further colour forming reaction. The compounds according to the invention are therefore comparable in this respect with the known white couplers which have been described, for example, in U.S. Pat. No. 2,998,314. On the other hand, however, this reaction releases a diffusible mercapto compound which is capable of inhibiting further development of the silver halide. The inhibiting action can be effective both in the layer which contains the compounds according to the invention, if it contains developable silver halide, and in adjacent silver halide emulsion layers into which the released inhibitor is capable of diffusing. In this way, the compounds according to the invention are capable of controlling development in each of the individual light-sensitive silver halide emulsion layers in numerous ways, and the neighbourhood effects which can be brought about by the componds according to the invention can be used to influence the development of one silver halide emulsion layer by the results of imagewise development in another layer so that an overall improvement can be obtained in graininess, sharpness and colour reproduction.

The light-sensitive silver halide emulsion layers of the photographic material according to the invention have differing spectral sensitivities and each is associated with at least one non-diffusible compound to produce an image dye with a colour which is generally complementary to the spectral sensitivity. These compounds may be conventional colour couplers which are generally incorporated in the silver halide layers themselves. Thus, the red-sensitive layer, for example, contains a non-diffusible colour coupler for production of the cyan partial colour image, generally a coupler of the phenol or α-naphthol series. The green sensitive layer contains at least one non-diffusible colour coupler for producing the magenta partial colour image, usually a colour coupler of the 5-pyrazolone or indazolone series. The blue-sensitive layer unit contains at least one non-diffusible colour coupler for production of the yellow partial image, generally a colour coupler with an open chain ketomethylene group. Colour couplers of these kinds are known in large number and have been described in numerous Patent Specifications. Reference is made particularly to the publication entitled "Farbkuppler" by W. PELZ in "Mitteilungen aus den Forschungslaboratorien der Agfa, Leverkusen/München", Volume III (1961), and to K. Venkataraman "The Chemistry of Synthetic Dyes", Vol. 4 341–387, Academic Press 1971.

The non-diffusible colour couplers may contain a releasable substituent in the coupling position so that, in contrast to the usual 4-equivalent couplers they require only two equivalents of silver halide to form the colour. The colour couplers used are generally themselves colourless but if the releasable substituent contains a chromophoric group, as in the known masking couplers, then the colour couplers generally have a colour which can be used for masking unwanted side densities of the image dye by conventional masking techniques. The image dyes produced from colour couplers are generally diffusion resistant.

The image dyes may, however, first be produced in a diffusible form by the development process and only fixed subsequently after transfer to an image-receiving layer as in the various dye diffusion transfer processes already known, e.g. according to U.S. Pat. No. 3,227,550, U.S. Pat. No. 3,628,952 and German Pat. No. 1,772,929. In these processes, colourless or coloured, non-diffusible dye-giving compounds from which diffusible dyes are released in imagewise distribution in the development process are associated with the light-sensitive silver halide emulsions. These dye-giving compounds are incorporated either with the silver halide emulsion layer or with an associated hydrophilic layer of binder which may, for example contain development nuclei and, if desired, also a silver halide which is capable of development without exposure.

If the usual silver halide emulsions are used in combination with non-diffusible colour couplers or with non-diffusible dye-giving compounds, negative colour images are normally produced. However, with the aid of the DIR compounds according to the invention it is possible, as with DIR couplers, to carry out reversal processes to produce positive images. This may be achieved, for example, if a silver halide emulsion layer which is capable of spontaneous development, i.e. without exposure, and which contains a colour coupler or dye-giving compound is arranged adjacent to a conventional silver halide emulsion layer which contains a DIR compound. It is obvious that such a procedure requires the use of DIR couplers or DIR compounds which liberate the inhibitor very rapidly so that it can inhibit development imagewise in the spontaneously developable layer.

The non-diffusible colour couplers and dye-giving compounds as well as the non-diffusible compounds used according to the invention which release a development inhibitor are added to the light-sensitive silver halide emulsions or other casting solutions by the usual, known methods. If the compounds are soluble in water or alkalies, they may be added to the emulsions in the form of aqueous solutions, optionally with the addition of water-miscible organic solvents such as ethanol, acetone or dimethylformamide. If the non-diffusible colour couplers, dye-giving compounds or development inhibitor releasing compounds are insoluble in water or alkalies, they may be emulsified in known manner, for example by mixing a solution of these compounds in a low boiling organic solvent either directly with the silver halide emulsion or first with an aqueous gelatine solution, and then evaporating off the organic solvent. The resulting emulsion of the compound in gelatine is then mixed with the silver halide emulsion. If desired, emulsification of these hydrophobic compounds may be assisted by the addition of so-called coupler solvents or oil forming agents, which are generally higher boiling organic compounds which form oily droplets which enclose the non-diffusible colour couplers and development inhibitor releasing compounds which are required to be emulsified in the silver halide emulsions. Reference is made in this connection, for example, to U.S. Pat. Nos. 2,322,027; 3,689,271; 3,764,336; 3,725,897 and 3,698,909. If the compounds according to the invention are emulsified in the layers with the aid of such oil forming substances, the groups which confer diffusion-resistance in the compounds according to the invention need not be so powerful, since in this case shorter alkyl groups, e.g. isoamyl groups, are occasionally sufficient to prevent diffusion of the compounds according to the invention in the layers of photographic material.

The usual silver halide emulsions may be used for the present invention. The silver halide contained in them may be silver chloride, silver bromide or mixtures thereof, optionally with a silver iodide content of up to 20 mols %. The emulsions may be usual negative emulsions or direct positive emulsions, e.g. emulsions which have a high sensitivity in the interior of the silver halide grains, for example those described in U.S. Pat. No. 2,592,250.

The binder used for the photographic layers is preferably gelatine, although this may be partly or completely replaced by other natural or synthetic binders. Suitable natural binders include, for example, alginic acid and its derivatives such as its salts, esters or amides, cellulose derivative such as carboxymethylcellulose, alkylcelluloses such as hydroxyethylcellulose, starch or its derivatives such as its ethers or esters, or carrageenates. Suitable synthetic binders include polyvinyl alcohol, partially saponified polyvinyl acetate, polyvinyl pyrrolidone and the like.

The emulsions may also be chemically sensitized. For example, sulphur compounds such as allyl isothiocyanate, allyl thiourea, sodium thiosulphate or the like may be added at the stage of chemical ripening. Reducing agents may also be added as chemical sensitizers, for example the tin compounds described in Belgian Pat. No. 493,464 or No. 568,687 or polyamines such as diethylene triamine or aminomethanesulphinic acid derivatives, e.g. according to Belgian Pat. No. 547,323.

Noble metals such as gold, platinum, palladium, iridium, ruthenium or rhodium and compounds of these metals are also suitable chemical sensitizers. This method of chemical sensitization has been described in the article by R. KOSLOWSKY, Z. Wiss. Phot. 46, 65–72 (1951).

The emulsions may also be sensitized with polyalkylene oxide derivatives, for example with a polyethylene oxide having a molecular weight of between 1000 and 20,000, or with condensation products of alkylene oxides and aliphatic alcohols, glycols, cyclic dehydration products of hexitols, alkyl substituted phenols, aliphatic carboxylic acids, aliphatic amines, aliphatic diamines or amides. The condensation products have a molecular weight of at least 700 and preferably more than 1000. These sensitizers may, of course, be combined to achieve special effects, as described in Belgian Pat. No. 537,278 and in British Pat. No. 727982.

The emulsions may also be spectrally sensitized, for example with the usual monomethine or polymethine dyes such as acid or basic cyanines, hemicyanines, streptocyanines, merocyanines, oxonoles, hemioxonoles, styryl dyes or others, including also trinuclear or higher nuclear methine dyes, for example rhodacyanines or neocyanines. Sensitizers of this kind have been described, for example, in the work by F.M. HAMER "The Cyanine Dyes and related Comounds" (1964), Interscience Publishers, John Wiley and Sons.

The emulsions may contain conventional stabilizers, e.g. homopolar or salt-type compounds of mercury which contain aromatic or heterocyclic rings such as mercapto triazoles, simple mercury salts, sulphonium mercury double salts and other mercury compounds. Azaindenes are also suitable as stabilizers, particularly tetra- or pentaazaindenes and especially those which are substituted with hydroxyl or amino groups. Compounds of this kind have been described in the article by BIRR, Z. Wiss. Phot. 47, 2–27 (1952). Other suitable stabilizers include, inter alia, heterocyclic mercapto compounds, e.g. phenylmercaptotetrazole, quaternary benzothiazole derivatives, benzotriazole and the like.

The emulsions may be hardened in the usual manner, for example with formaldehyde or halogen-substituted aldehydes which contain a carboxyl group, such as mucobromic acid, diketones, methane sulphonic acid esters, dialdehydes carbodiimides, carbamoylpyridinium salts and carbamoyloxypyridinium salts.

EXAMPLES

The DIR compounds are preferably used in multilayered arrangements of the kind which are conventionally used, for example, for the preparation of light-sensitive colour photographic materials which operate negatively or positively.

The effect of the DIR-compounds according to the invention will be demonstrated with the aid of an arrangement of layers which is typical or colour negative materials, or with partial layers thereof. Light-sensitive photographic material:

Arrangement of layers

Support: Cellulose triacetate support with substrate.
(a) Intermediate layer of gelatine (1μ)
(b) Cyan layer consisting of an emulsion sensitized to the red spectral region and a colour coupler for cyan (silver application: 4 g Ag/m$^2$);
(c) Intermediate layer of gelatine (1μ);
(d) Magenta layer consisting of an emulsion sensitized to the green spectral region and a colour coupler for magenta (silver application: 3.5 g of Ag/m$^2$;
(e) Intermediate layer of gelatine (1μ);
(f) Yellow filter layer (2μ);
(g) Yellow layer consisting of an emulsion sensitized to the blue spectral region and a colour coupler for yellow (silver application: 1.5 g of Ag/m$^2$;
(h) Protective layer of gelatine (1μ).

The material is hardened in the usual manner, for example with tris-acryloyl-hexahydrotriazine. The individual partial layers which are sensitive to red (b), green (d) and blue (g) are prepared by casting the following solutions:

(b) 1 kg of a silver halide emulsion which has been sensitized for red (100 g of Ag/kg of emulsion) and in which the silver halide consists of 98 mols % of silver bromide and 2 mols % of silver iodide, 50 ml of a 1% solution of 4-hydroxy-6-methyl-1,3,3a,7-tetraazaindene in methanol, 240 g of a coupler dispersion of a solution of 15 g of the cyan coupler of the following formula:

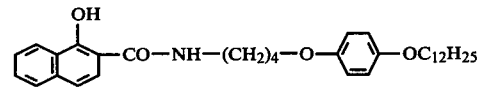

in 7.5 g of dibutylphthalate and
30 g of diethylcarbonate,
100 ml of a 4% aqueous gelatine solution,
0.8 g of Mersolat ® (wetting agent, sulphated paraffin hydrocarbons),
10 ml of a 10% aqueous saponin solution, and 1000 ml of water.

(d) The composition of the casting solution for the green sensitive layer corresponds to that of the red sensitive layer b) with the exception that the emulsion is sensitized for the green region of the spectrum and instead of the cyan coupler dispersion it contains 150 g of a dispersion of the magenta coupler of the following formula:

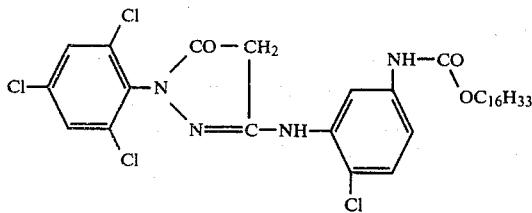

in a composition similar to that used for the cyan emulsion in layer b).

(g) The composition of the casting solution for the yellow layer corresponds to that of the red sensitive layer (b) with the exception that the emulsion is sensitized only to the blue region of the spectrum and instead of the cyan coupler dispersion it contains 175 g of a 5% solution of the yellow coupler of the following formula:

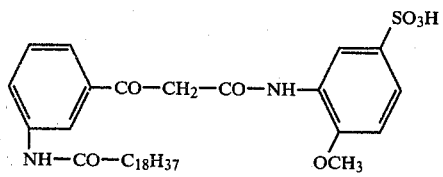

in an aqueous 8% gelatine solution.

The gelatine layers a, c, e, and h are prepared by casting the following solution:
125 ml of a 10% gelatine solution,
500 ml of water, and
5 ml of a 10% aqueous solution of saponin.

The casting solution for the yellow filter layer is identical to the casting solution for the gelatine layers a, c, e and h except for the addition of 1.4 g of finely dispersed metallic silver of the kind commonly used as a barrier filter for the blue spectral portion of light.

Processing

The material is exposed successively behind the colour separation filters blue, green and red and behind a grey step wedge in a conventional sensitometer. After exposure the material is developed in a colour developer of the following composition:
2 g of the sodium salt of isopropanoldiaminotetracetic acid,
30 g of potassium carbonate
4 g of potassium sulphite,
1.5 g of KBr,
2 g of hydroxylamine, and
5 g of the colour developer of the following formula:

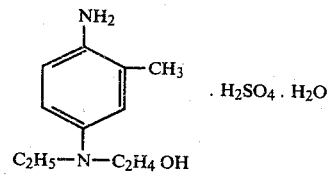

made up to 1 liter. pH adjusted to 10.2.
Development: 5 minutes at 25° C.
The subsequent stages of processing described below take 8 minutes in each case. The bath temperatures employed are also 25° C.

Short stop bath: 30 ml of acetic acid (concentrated), 20 g of sodium acetate, and water up to 1 liter.
Washing
Bleaching bath: 100 g of potassium ferricyanide, 15 g of potassium bromide, and water up to 1 liter.
Washing
Fixing bath: 20% aqueous solution of sodium thiosulphate
Final wash.

EXAMPLE 1

Incoporation of DIR compound 1 in red sensitive layer b. The DIR compound 1 is dispersed as follows:

A solution of 6 g of compound No. 1 in 3 g of tricresyl phosphate and 12 ml of ethyl acetate is emulsified in a solution of 100 ml of a 4% aqueous gelatine solution and 0.8 g of Mersolat ® (wetting agnet; sulphated paraffin hydrocarbons) with vigorous stirring, using a mixing siren. Arrangement of layers: consisting of layers a, b and c.

Sample 1: No DIR compound in layer b
Sample 2: Layer b contains DIR compound 1. The dispersion of DIR compound 1 is added to the casting solution for the layer in an amount of 90 g to every 1 kg of emulsion.

The samples are exposed to red light behind a step wedge and developed as described above. The inhibition produced by the DIR compound reduces the gradation from $\gamma = 1.37$ (Sample 1) to $\gamma = 0.7$ (Sample 2). If in one portion of the comparison sample which is free from DIR compound (Sample 1 a) and quantities of silver halide and colour coupler are reduced so that the gradation is also reduced to $\gamma = 0.7$, then the graininess of sample 2 which contains DIR compound is found to be substantially lower than in sample 1 as in spite of the fact that the two samples have the same gradation.

|  | Sample 1 a | Sample 2 |
|---|---|---|
| Graininess $\sigma D \cdot 10^{-2}$ at density $D = 1$ | 2.0 | 1.2 |

The graininess is given in $\sigma_D$-values (r.m.s. values at a diaphragm aperture diameter of $29\mu$) according to the method described by H. T. Buschmann in "Bestimmung der Körnigkeit photographischer Schichten mit Hilfe digitaler Technik" in Optik 38, 1973, pages 169–219.

EXAMPLE 2

Incorporation of DIR compound 4 in the gelatine intermediate layer c.

The DIR compound 4 is emulsified as described in Example 1.

A complete arrangement of layers (layers a to h) is prepared in which the DIR compound 4 is incorporated in the gelatine intermediate layer c, in other words between the red-sensitive and the green-sensitive layer (Sample 1).

The casting solution for the modified gelatine layer c has the following composition:
50 ml of a 10% gelatine solution,
100 g of an emulsion of DIR compound 4,
500 g of water, and
7 ml of a 10% aqueous solution of saponin.
Layer c is applied in a thickness of $1.5\mu$.

For comparison, a complete arrangement of layers containing the normal gelatine intermediate layer c is prepared (Sample 2).

The samples are exposed to red, green and white light behind a step wedge and processed as described above.

The results show that accidental development of the magenta layer d which occurs to a certain extent in Sample 2 on exposure to red light, i.e. on development of the cyan layer b, is completely prevented by the presence of the DIR compound. In the same way, the DIR compound in the intermediate layer c also completely prevents accidental development of the cyan layer d on exposure to green light, i.e. on development of the magenta layer d. The DIR compound absorbs the developer oxidation product diffusing from adjacent layers by undergoing a coupling reaction with it. This reaction releases an inhibitor which diffuses into the adjacent red-sensitive and green-sensitive layers to inhibit development in these layers. An inter image effect (IIE) is thereby produced which may be defined as follows:

$$IIE = \frac{\gamma_s - \gamma_w}{0.6} \cdot 100[\%]$$

s = selective exposure
w = white exposure

Since the layers of this experimental photographic material are not masked, the side densities of the dyes interfere with the determination of the true IIE. To eliminate the interferring effect of the side densities, the gradation curves are drawn up from the analytical densities determined by converting the measured densities. The $\gamma$-values were obtained from these gradation curves.

|  | IIE | | Red exposure cyan$\gamma_s$ | Green exposure magenta $\gamma_s$ | White exposure | |
| --- | --- | --- | --- | --- | --- | --- |
|  | Cyan | Magenta | | | cyan $\gamma_w$ | magenta $65_w$ |
| Sample 1 | 77% | 47% | 1.02 | 0.82 | 0.56 | 0.60 |
| Sample 2 | 30% | 20% | 1.30 | 1.20 | 1.12 | 1.08 |

The Table clearly shows that the DIR compound incorporated in the gelatine intermediate layer c considerably increases the IIE both in the cyan layer and in the magenta layer.

EXAMPLE 3

Incorporation of DIR compounds in the magenta layer (d) of total layer arrangements (layers a to h). The DIR compounds 3, 10, 11, 12, 15, 16, 17 (and for comparison) A, B, C, D, E, F, H and I are emulsified in comparable molar quantities as described in Example 1. The DIR compounds 13 and 14 are dissolved in alkaline water, the DIR-compound G in water at 60° C. and added to the emulsion at 50° C. Comparable molar quantities of dispersions or solutions of the DIR compounds are added to the casting solution of layer d (e.g. in the case of Sample 1, DIR compound No. 3, 100 g of dispersion to 1 kg of silver halide emulsion).

The samples are exposed to red, green and white light behind a step wedge and developed as described above. Since the film is not masked, the analytical densities are used to draw up the gradation curves.

The activity of the DIR compounds can be seen from the magenta δ values of green exposure (magenta $\delta_s$). The effect of the DIR compound contained in the magenta layer on the IIE of the cyan layer was also investigated.

| Sample | DIR compound | IIE cyan | Exposure red cyan $\gamma_s$ | green magenta $\gamma_s$ | white cyan $\gamma_w$ |
| --- | --- | --- | --- | --- | --- |
| 1 | 3 | 80% | 1,38 | 0,75 | 0,90 |
| 2 | 10 | 83% | 1,37 | 0,70 | 0,87 |
| 3 | 11 | 70% | 1,39 | 0,81 | 0,97 |
| 4 | 12 | 90% | 1,35 | 0,65 | 0,81 |
| 5 | 13 | 79% | 1,40 | 0,72 | 0,93 |
| 6 | 14 | 98% | 1,34 | 0,62 | 0,75 |
| 7 | 15 | 78% | 1,38 | 0,73 | 0,91 |
| 8 | 16 | 75% | 1,40 | 0,79 | 0,95 |
| 9 | 17 | 85% | 1,33 | 0,69 | 0,82 |
| 10 | A | 28% | 1,37 | 1,20 | 1,20 |
| 11 | B | 32% | 1,37 | 1,19 | 1,18 |
| 12 | C | 43% | 1,38 | 1,09 | 1,12 |
| 13 | D | 28% | 1,36 | 1,21 | 1,19 |
| 14 | E | 50% | 1,35 | 1,01 | 1,05 |
| 15 | F | 47% | 1,35 | 1,05 | 1,07 |
| 16 | G | 55% | 1,37 | 1,00 | 1,04 |
| 17 | H | 48% | 1,36 | 1,04 | 1,07 |
| 18 | I | 42% | 1,35 | 1,08 | 1,10 |
| 19 | — | 32% | 1,39 | 1,22 | 1,20 |

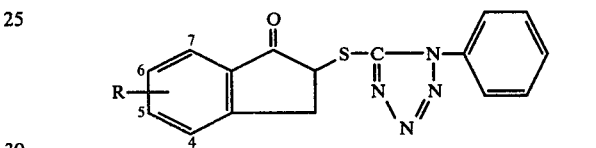

| DIR compound | R = |
| --- | --- |
| A | 5-O—(CH$_2$)$_{15}$—CH$_3$ |
| B | 6-NH—SO$_2$—(CH$_2$)$_{15}$—CH$_3$ |
| C | 6-NH—COO—(CH$_2$)$_{11}$—CH$_3$ |
| D | 5-NH—CO—(CH$_2$)$_4$—O—⟨phenyl⟩—C$_5$H$_{11}$tert. / C$_5$H$_{11}$tert. |
| E | 5-NH—SO$_2$—(CH$_2$)$_{15}$—CH$_3$ |
| F | 5-NH—COO—(CH$_2$)$_{11}$—CH$_3$ |
| G | 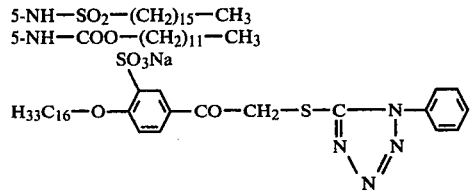 |

(German PS No. 1 547 640, Compound 73)

| H | 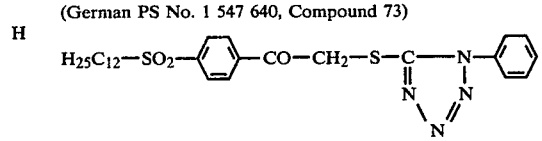 |

(according to German PS No. 1 547 640)

| I | 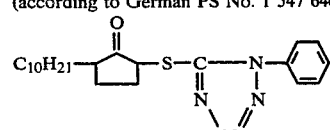 |

(German OS No. 2 359 295, Compound 7)

It is clear from the Table (magenta $\delta_s$) that the DIR compounds 3, 10, 11, 12, 13, 14, 15, 16, 17 (Samples 1 to 9 inhibit the development in the magenta layer most powerfully. The other DIR compounds are much less active. When the film is exposed to white light, the inhibitor which is released from DIR compounds in samples 1 to 9 on development in the magenta layer and diffuses into the cyan layer also powerfully inhibits development of the cyan layer, so that a stron cyan IIE (up to 98%) is produced. The IIE in the adjacent cyan layer, which is present even without a DIR coupler (Sample 19), is much less increased by the other DIR compounds.

We claim:

1. In a color photographic material containing in at least one of its lightsensitive silver halide emulsion layers or a non lightsensitive binder layer associated with one of said lightsensitive silver halide emulsion layers, a non-diffusing thioether compound capable of releasing on reaction with the oxidation product of a color developer compound a diffusing mercapto compound which inhibits the further development of the silver halide, wherein the improvement comprises the thioether compound corresponds to the following formula

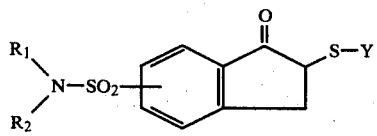

wherein

Y represents a non-coupling radical selected from the group consisting of an aliphatic radical, an aromatic radical and a heterocyclic radical, splittable together with the sulfur atom of the thioether bridge to form a diffusible mercapto compound capable of inhibiting silver halide development, $R_1$ represents hydrogen or an alkyl group having 1–3 carbon atoms, and $R_2$ represents an alkyl group having up to 22 carbon atoms including a photographic inert group providing resistance to diffusion, or an aralkyl group or an aryl group carrying a photographic inert group providing resistance to diffusion.

2. A material as claimed in claim 1 comprising separated by non-lightsensitive binder layers, at least a red-sensitive silver halide emulsion layer, a green sensitive silver halide emulsion layer and a blude sensitive silver halide emulsion layer and containing associated with each of said red sensitive, green sensitive and blue sensitive silver halide emulsion layers a non-diffusing coupler or dye-giving compound which on color development yields a non-diffusing or diffusing image dye of a color which is essentially complementary of the sensitivity of the associated silver halide layer, which material contains in at least one of its lightsensitive silver halide emulsion layers or non-lightsensitive binder layers a non-diffusing thioether compound capable of releasing on reaction with the oxidation product of a color developer compound a diffusing mercapto compound which inhibits the further development of the silver halide, wherein the improvement comprises the thioether compound corresponds to the following formula

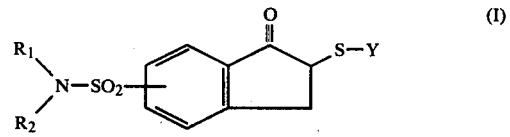

wherein

Y represents a non-coupling radical selected from the group consisting of an aliphatic radical, an aromatic radical and a heterocyclic radical, splittable together with the sulfur atom of the thioether bridge to form a diffusible mercapto compound capable of inhibiting silver halide development, $R_1$ represents hydrogen or an alkyl group having 1–3 carbon atoms, and $R_2$ represents an alkyl group having up to 22 carbon atoms including a photographic inert group providing resistance to diffusion, or an aralkyl group or an aryl group carrying a photographic inert group providing resistance to diffusion.

3. A material as claimed in claim 2 which contains said non-diffusing thioether compound in the red sensitive silver halide emulsion layer and/or the green sensitive silver halide emulsion layer and/or a non-light sensitive binder layer between said red sensitive and green sensitive layers.

4. A material as claimed in claim 1, in which in the formula of claim 1 Y represents an 1-aryl-tetrazole radical.

5. A material as claimed in claim 1, in which in the formula of claim 1 the group

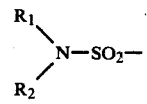

is attached to the 5- or 6-position of the indanone group.

* * * * *